United States Patent
Anderson et al.

(10) Patent No.: US 10,925,208 B2
(45) Date of Patent: Feb. 23, 2021

(54) SYSTEM AND METHOD FOR MONITIORING VAPOR CONCENTRATIONS

(71) Applicant: Deere & Company, Moline, IL (US)

(72) Inventors: Noel W. Anderson, Fargo, ND (US); Ramanathan Sugumaran, Moline, IL (US)

(73) Assignee: Deere & Company, Moline, IL (US)

( * ) Notice: Subject to any disclaimer, the term of this patent is extended or adjusted under 35 U.S.C. 154(b) by 286 days.

(21) Appl. No.: 16/016,584

(22) Filed: Jun. 23, 2018

(65) Prior Publication Data

US 2019/0124825 A1  May 2, 2019

Related U.S. Application Data

(60) Provisional application No. 62/579,854, filed on Oct. 31, 2017.

(51) Int. Cl.
*A01C 21/00* (2006.01)
*A01C 23/00* (2006.01)
(Continued)

(52) U.S. Cl.
CPC .......... *A01C 21/007* (2013.01); *A01B 49/06* (2013.01); *A01C 21/005* (2013.01);
(Continued)

(58) Field of Classification Search
CPC ... A01C 21/007; A01C 23/007; A01C 21/005; A01C 23/024; A01B 49/06; G01N 33/24;
(Continued)

(56) References Cited

U.S. PATENT DOCUMENTS 9,532,499 B2    1/2017  Anderson et al.
9,740,208 B2    8/2017  Sugumaran et al.
(Continued)

FOREIGN PATENT DOCUMENTS

CN    206417189 U    8/2017
WO    2017095475 A1  6/2017

OTHER PUBLICATIONS

Bretschneider, Timo Rolf and Shetti, Karan. "UAV-based Gas Pipeline Leak Detection." ResearchGate [online conference paper] Oct. 2014. Published Apr. 17, 2015 [retrieved on Jun. 21, 2018]. Retrieved from the Internet <URL: https://www.researchgate.net/publication/275035983_UAV-based_gas_pipeline_leak_detection>.

(Continued)

*Primary Examiner* — Frederick M Brushaber
(74) *Attorney, Agent, or Firm* — Hanley, Flight & Zimmerman, LLC

(57) ABSTRACT

A sensor system for monitoring vapor concentrations associated with an agricultural implement is disclosed. The sensor system comprises a first sensor coupled to a support structure that is configured to sense a concentration of at least one component of a vapor sample associated with dispensed ammonia that is emitted from the soil. A controller is communicatively coupled to the first sensor, and is configured to receive and process output signals generated by the first sensor to determine an amount of the concentration of the at least one component that is loss during emission.

20 Claims, 7 Drawing Sheets

(51) Int. Cl.
*A01B 49/06* (2006.01)
*G01N 33/24* (2006.01)
*G08B 21/18* (2006.01)
*A01C 23/02* (2006.01)
*G01N 33/00* (2006.01)
*B64C 39/02* (2006.01)

(52) U.S. Cl.
CPC .......... *A01C 23/007* (2013.01); *A01C 23/024* (2013.01); *G01N 33/0054* (2013.01); *G01N 33/24* (2013.01); *G08B 21/182* (2013.01); *B64C 39/024* (2013.01); *B64C 2201/12* (2013.01); *G01N 2033/245* (2013.01)

(58) Field of Classification Search
CPC ......... G01N 33/0054; G01N 2033/245; G08B 21/182; B64C 39/024; B64C 2201/12
See application file for complete search history.

(56) References Cited

U.S. PATENT DOCUMENTS

| | | | | |
|---|---|---|---|---|
| 9,936,442 B1* | 4/2018 | Noonan | .................... | C10G 2/33 |
| 2015/0373905 A1* | 12/2015 | Anderson | .............. | A01C 21/00 |
| | | | | 701/50 |
| 2016/0169855 A1 | 6/2016 | Baity | | |
| 2016/0368604 A1* | 12/2016 | Duesterhoft | ............. | B64D 1/02 |
| 2016/0370263 A1* | 12/2016 | Duesterhoft | ............. | B64D 1/02 |
| 2017/0115218 A1* | 4/2017 | Huang | .................... | G01S 17/06 |
| 2017/0227676 A1* | 8/2017 | Archer | .................... | G01N 33/24 |
| 2017/0363541 A1 | 12/2017 | Sandsten et al. | | |
| 2018/0292374 A1* | 10/2018 | Dittberner | ............ | G08G 5/0039 |
| 2020/0026253 A1* | 1/2020 | Fuhr | .................... | H04L 9/3297 |
| 2020/0124584 A1* | 4/2020 | Morgan | ................ | G01N 33/24 |
| 2020/0182779 A1* | 6/2020 | Kasten | ............... | G01N 21/3103 |

OTHER PUBLICATIONS

May, Randy D. "Open-path, near-infrared tunable diode laser spectrometer for atmospheric measurements of H20" Journal of Geophysical Research: Atmospheres, vol. 103, No. D15; pp. 19,161-19,172; published Aug. 20, 1998 [retrieved on Jun. 21, 2018]. Retrieved from the Internet <URL: https://agupubs.onlinelibrary.wiley.com/doi/epdf/10.1029/98JD01678>.

Tarantola, Andrew. "NASA's flying methane meter built for Mars finds work on Earth." Gadgetry, published Mar. 28, 2016 [online article] [retrieved on Jun. 21, 2018]. Retrieved from the Internet <URL: https://www.engadget.com/2016/03/28/nasa-s-flying-methane-meter-built-for-mars-finds-work-on-earth/.

Unpublished U.S. Appl. No. 15/865,553, filed Jan. 9, 2018, Barker et al., (57 pages).

Search Report issued in counterpart application No. EP18202951.2, dated Mar. 22, 2019 (9 pages).

\* cited by examiner

US 10,925,208 B2

SYSTEM AND METHOD FOR MONITORING VAPOR CONCENTRATIONS

TECHNICAL FIELD

The present disclosure generally relates to a system and method for monitoring vapor concentrations associated with an agricultural implement.

BACKGROUND

When planting crops that are ultimately used to aliment the population it is necessary ensure that the process is not interrupted. Anhydrous ammonia (NH3), or simply ammonia, is a commercially available source of nitrogen fertilizer which helps plants grow; therefore, is widely used in the commercial production of crops like maize or corn. Unfortunately, ammonia can be released into the atmosphere during the application process, resulting in a difficult and, at times, severe reduction of yields for crop during a growing season. Therefore, there is a need for accurate level measurement of ammonia.

For example, in conventional anhydrous ammonia application, there are two common but imprecise approaches to monitoring NH3 vaporization. In the first, ammonia has a distinct odor which may be detected by a human operator. However, operator cab air filtration and wind dissipation of NH3 vapor may result in the operator not accurately gauging the NH3 escape or missing it altogether. In the second, NH3 vapor is much colder than ambient air. As it escapes, it causes water in the air to condense, forming a visible cloud. This method is also unreliable in that it requires certain relationships between NH3 and air temperature as well as humidity. Wind may also disperse the vapor and water cloud, making it hard to gage the amount of NH3 escaping. Thus, while NH3 meters can provide the gross amount of nitrogen applied to the soil, the net amount cannot be determined without an accurate measure of NH3 lost to the atmosphere at application. In the least, there still exists a need for detecting and reporting excessive loss of NH3 to the air. Insufficient nitrogen fertilization can result in reduced crop yield.

SUMMARY

According to an aspect of the present disclosure, a sensor system for monitoring vapor concentrations that is associated with an agricultural implement is disclosed. The sensor system can comprise a first sensor coupled to a support structure that is configured to sense a concentration of at least one component of a vapor sample emitted from the soil, where the vapor sample is associated with the dispensed ammonia. A controller is communicatively coupled to the first sensor. The controller is configured to receive and process output signals generated by the first sensor to determine an amount of the concentration of the at least one component that is lost during emission, and if the loss exceeds a certain threshold level, an alert is displayed or communicated to an operator of the implement.

Other features and aspects will become apparent by consideration of the detailed description and accompanying drawings.

BRIEF DESCRIPTION OF THE DRAWINGS

Like reference numerals are used to indicate like elements throughout the several figures.

DETAILED DESCRIPTION

Figure 1:
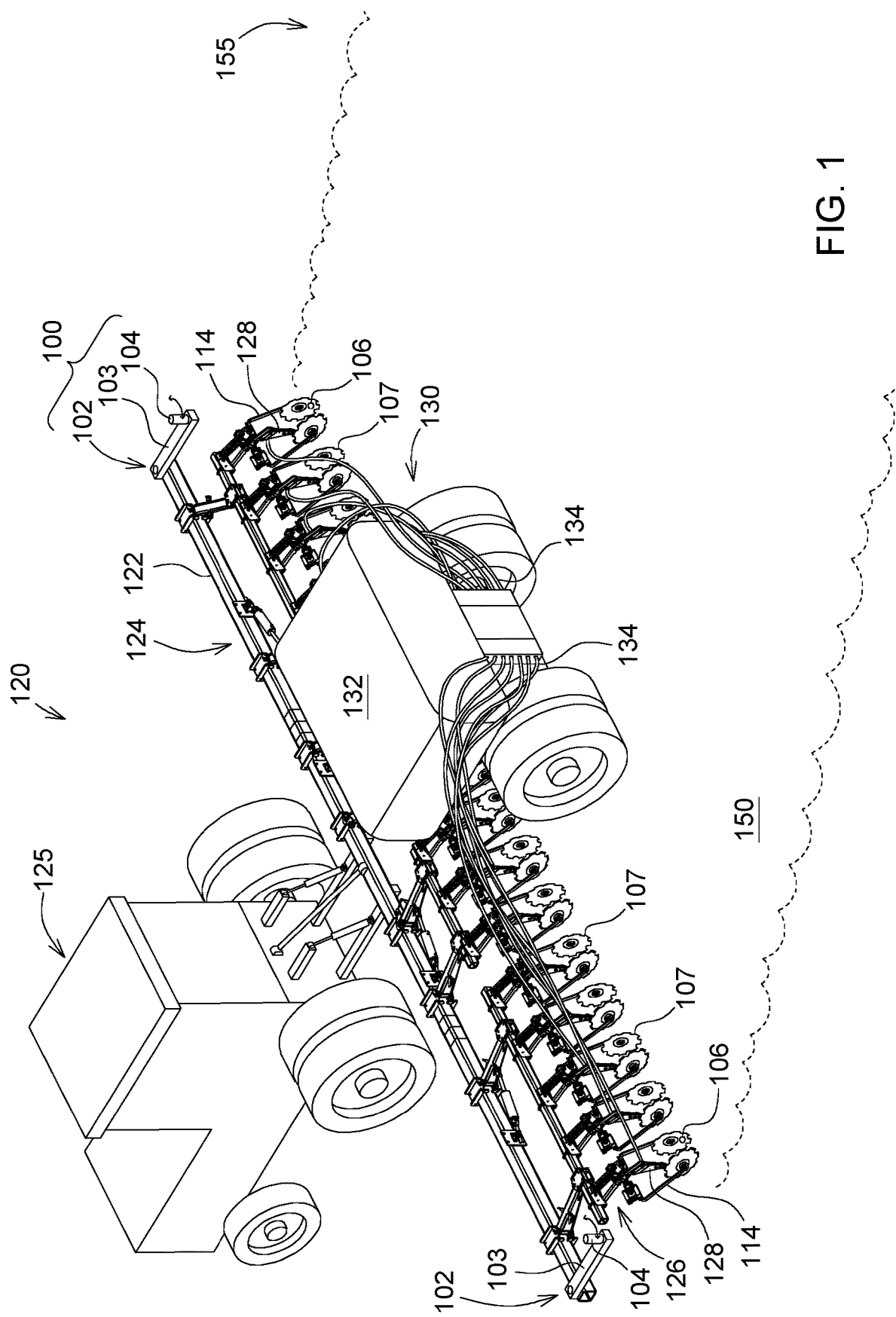
FIG. 1 is a perspective view of an exemplary embodiment of a sensor system for monitoring vapor concentrations associated with an implement in use.
Figure 2:
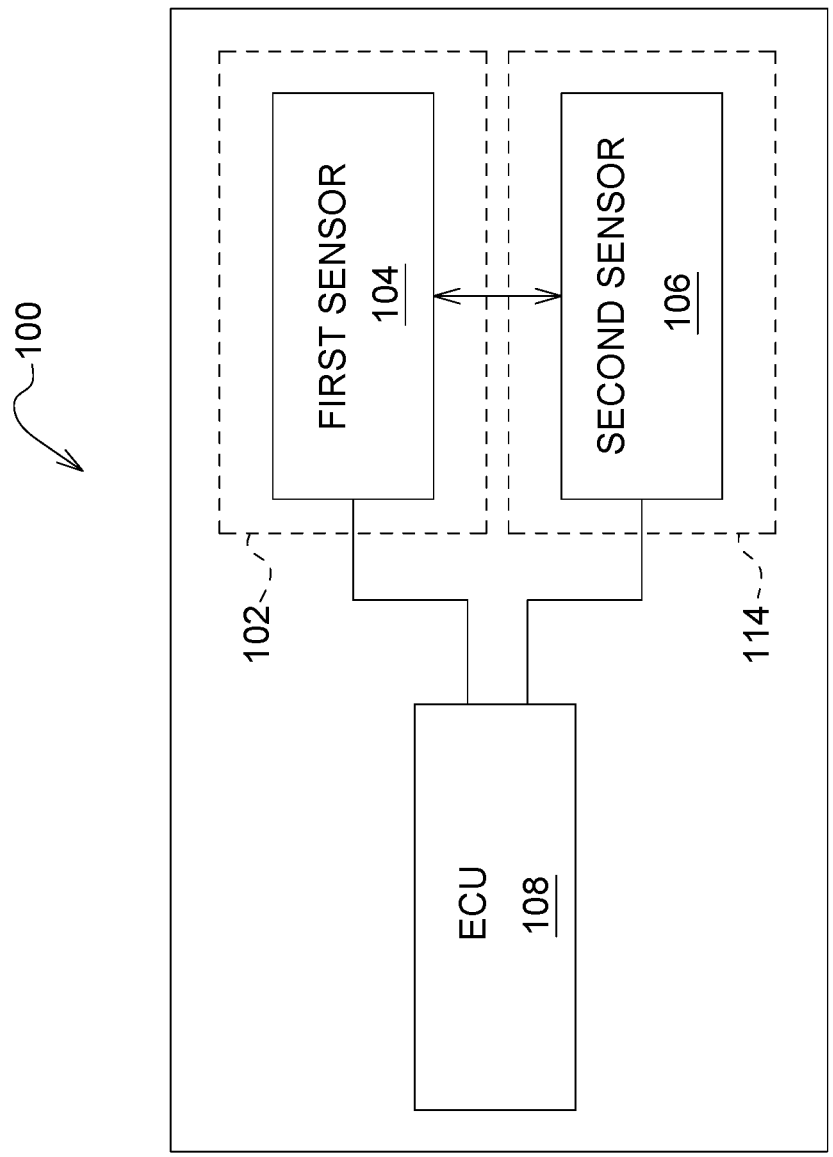
FIG. 2 is a block diagram of the sensor system of FIG. 1 according to an embodiment.

Referring to FIGS. 1-2, an agricultural apparatus 120 having a sensor system 100 incorporated therein is shown according to an embodiment. As depicted, the agricultural apparatus 120 can include an agricultural vehicle 125 that is arranged to tow an agricultural implement 124 across a worksite 155. The agricultural implement 124 can comprise a plurality of ground engaging elements 114 attached to a frame 122. The plurality of ground engaging elements 114 can be mechanically coupled to the agricultural implement 124 and can be arranged to extend downwardly from the agricultural implement 124 to perform soil cultivating tasks such as creating openings (e.g., holes, slivers, slices, trenches or furrows) in the soil 150 of worksite 155. Although the exemplary embodiments herein depict the ground engaging elements 114 as including closing wheels (e.g., serrated closing wheels), it should be noted that, in other embodiments, the ground engaging elements 114 can include disk harrows, coulters, opener disks, shanks, or other suitable elements, such as opener disks that are used to open the soil for dispensing ammonia or fertilizer in association with the applicator unit 126.

In addition to the ground engaging elements 114, an applicator unit 126 can be removably coupled, e.g., attached behind or underneath, the agricultural implement 124 with respect to the direction of travel of the agricultural vehicle 125. The applicator unit 126 can include a plurality of applicator devices 128 (e.g., nozzles or nutrient knives) that are arranged proximate the ground engaging elements 114 to direct crop input materials or other materials (e.g., anhydrous ammonia, nitrogen, fertilizer, fungicides, nutrients or any combination of crop inputs) into the soil 150 simultaneously as it is being prepared or cultivated. For example, if the applicator devices 128 comprise nutrient knives, the nutrient knives, alone or together with an opener or opener disk, may create a furrow or groove in the soil for accepting the ammonia or nitrogen, whereas the closer, serrated wheels, or other trailing devices 107 cover the furrow with soil. In various embodiments, the applicator devices 128 can include tubular, conical, funnel-shaped, syringe or other suitable dispenser shapes that are configured to accurately apply the crop input materials to small areas (e.g. within approximately 1-2 inches of a desired location). Further, it should be noted that depending on the size and span-width of the agricultural vehicle 110, one or more applicator units 126 can be attached to the rear of the agricultural vehicle 110, either in the lateral direction (e.g. perpendicular to direction of travel) or in series such as when there are multiple types of nutrients that are not mixed together. In other embodiments, the applicator unit 126 can be arranged to follow a field planter or seeder or no-till air drill (not shown) that is configured to perform a task such as putting seeds into selected positions in rows of soil and covering the seeds with soil. In this configuration, the subsequent applicator unit 126 releases or sprays crop inputs, ammonia, or other compounds near the seeds in a region adjacent to where the seeds are planted.

In some embodiments, an application system 130 can be arranged to trail rearward of the agricultural vehicle 125 and the agricultural implement 124 as shown in FIG. 1. In other embodiments, the application system 130 can be arranged on the agricultural vehicle 125 forward of the agricultural implement 124. The application system 130 can comprise a reservoir 132 (e.g., a tank or nurse tank) having a plurality of dispensing elements 134 coupled thereto that are arranged to supply the crop input materials to each of the applicator devices 128. In some embodiments, the reservoir 132 can contain pressurized ammonia, anhydrous ammonia ($NH_3$), or other suitable materials, which can be selected based on a desired farming application. For example, in other embodiments, the application system 130 can comprise an additional reservoir with corresponding dispensing elements 134 that is configured to supply a secondary crop input such as a fungicide, pesticide, herbicide, miticide, or other crop treatments.

The sensor system 100 can be arranged on or proximate the agricultural implement 124. In some embodiments, the sensor system 100 can comprise a support structure 102, a first sensor 104 arranged on the support structure 102, a second sensor 106 arranged on a respective ground engaging element 114, and a controller 108 communicatively coupled to the first and second sensors 104, 106. In some embodiments, the support structure 102 can comprise a support arm 103 removably or fixedly coupled to the agricultural implement 124 that is arranged to extend backwards and away from the agricultural implement 124 (FIG. 1), but may vary in other embodiments. The length of arm 103 illustrated in FIG. 1 is not necessarily scaled with respect to the other elements of FIG. 1 and may be longer in practice, such that the arm 103 extends above, near or behind the trailing ground engaging elements 114 In other embodiments, the support structure 102 can comprise an unmanned aerial vehicle 218, which can be coupled to or arranged to aerially suspend proximate the agricultural implement 124 as will be discussed in further detail with reference to FIG. 3.

As depicted in FIG. 1, in some embodiments, the first sensor 104 can comprise one or more sensors mounted on the support structure 102 proximate a vapor emission area, such as above, near or behind the trailing ground engaging elements 114. For example, the first sensor 104 can be pivoted on arm 103 to be readily located or re-located anywhere near the anhydrous NH3 source as conditions change or a need arises. The first sensor 104 can be configured to sense a concentration of at least one component of a vapor sample emitted from the soil 150 as the crop input materials are applied by the applicator devices 128. In various embodiments, the first sensor 104 can comprise a variety of sensors capable of measuring vapor concentrations, such as, for example, piezoelectric sensors, ultrasonic sensors, infrared sensors, acoustic sensors, laser spectrometers, non-equilibrium electrochemical principal, and other suitable sensor devices, or combinations thereof.

In some embodiments, an optional second sensor 106 may be used on the implement mounted on a pole or support extending above the trailing device. For instance, the optional second sensor 106 may include a soil attribute sensor, which can be arranged to look downward at the soil without contact with the soil or engage with the soil 150 to sense one or more attributes of a field or a crop over which the agricultural vehicle 112 is traveling. For example, the second sensor 106 can be configured to sense a variety of soil and crop-related properties such as, soil type, soil moisture, soil temperature, bulk soil density, soil organic matter, soil cover, residue density, crop type, weed presence, weed type, plant size, plant height, plant health, plant vigor, chemical presence, chemical distribution, or combinations thereof. In various embodiments, the second sensor 106 can be arranged above ground and can include, but is not limited to one or more of the following sensors: cameras, infrared cameras or other infrared sensors, video cameras, stereo cameras, optical sensors, LIDAR sensors, or structured light systems. Additionally, in other embodiments, the second sensor 106 can be arranged for in-ground measuring of the various soil and crop-related properties and can also include one or more of the aforementioned sensors.

The controller 108 can be arranged locally on the support structure (e.g., when the unmanned vehicle is used) or the agricultural vehicle 125. Additionally, in other embodiments, the controller 108 can be arranged remotely at a central data processing center. The controller 108 may include a microprocessor, microcontroller or other suitable programmable circuitry that is adapted to perform data processing and/or system control operations. For example, based on the measured sensor data received by each of the first and sensors 104, 106, the controller 108 can be configured to generate an operator alert, via the user interface module 506 (in FIG. 6), in response to a detected sensor concentration that exceeds a certain threshold level. In some embodiments, first and second sensors 104, 106 may communicate directly with each other.

As will be appreciated by those skilled in the art, FIGS. 1-2 are provided merely for illustrative and exemplary purposes and are in no way are intended to limit the present disclosure or its applications. In other embodiments, the arrangement and/or structural configuration of sensor system 100 can and will vary according to design and/or specification requirements. For example, in some embodiments, one or more additional first or sensors 104, 106 can be used to measure concentrations of other vapor materials, other soil or crop-related properties, as well as to provide zone specific measurements. Further, in other embodiments, the support structure 102 can comprise a plurality of unmanned aerial vehicles deployed near the agricultural implement 124 that are arranged to cover a specific zone or portion of the total vapor concentration area of interest. In yet other embodiments, the plurality of unmanned aerial vehicles could also be deployed to increase the frequency in which a spatial zone is measured.

Figure 3:
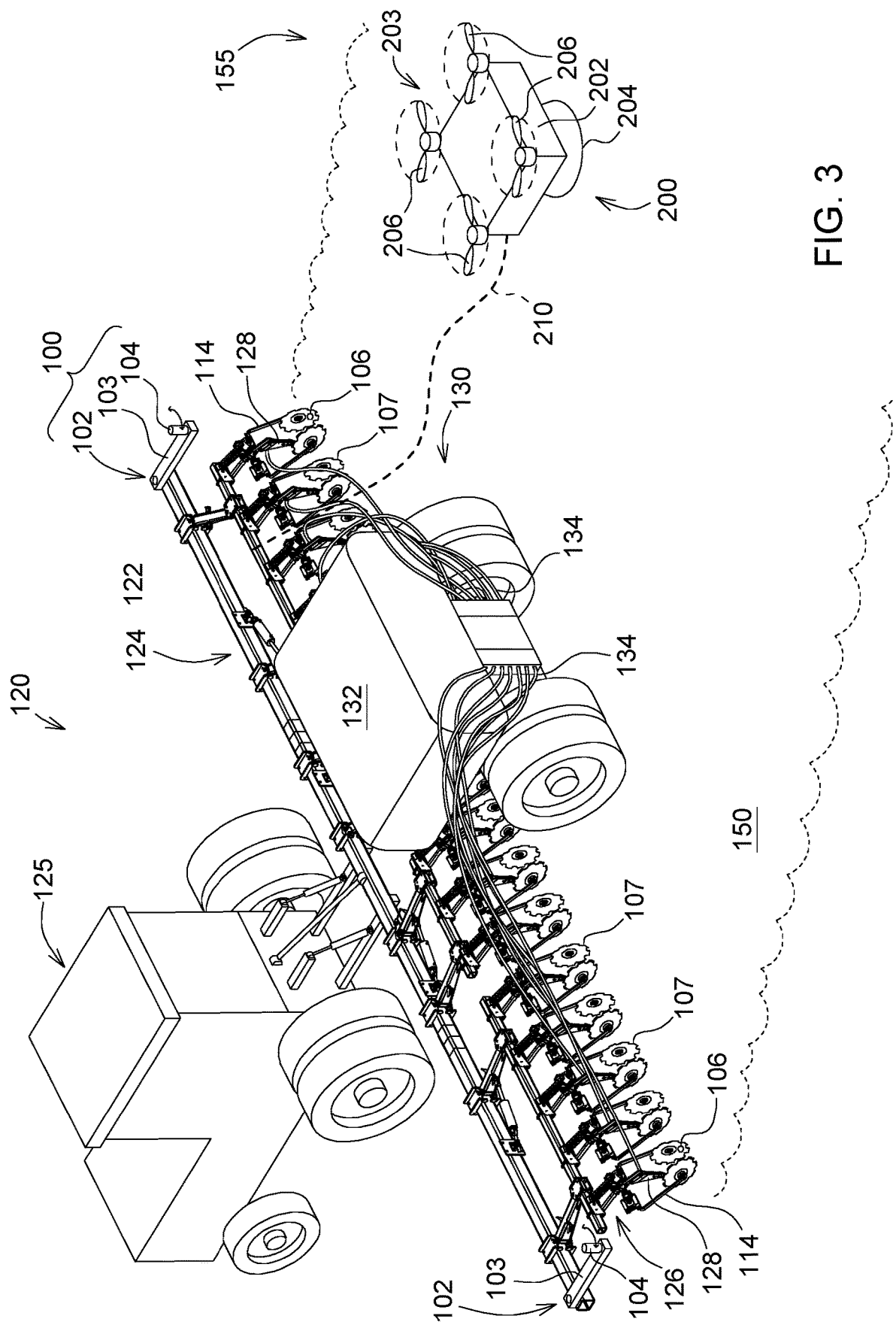
FIG. 3 is a perspective view of another exemplary embodiment of a sensor system for monitoring vapor concentrations associated with an implement in use.

Referring now to FIG. 3, an agricultural apparatus 120 having a sensor system 200 incorporated therein is shown according to an embodiment. Sensor system 200 is substantially to sensor system 100, however, sensor system 200 provides for improved measurement accuracy through the use of multiple sensor arrangements for the first sensor 104. For example, in sensor system 200 the first sensor 204 can be collectively arranged on both a support arm 103 and an unmanned aerial vehicle 203. In this exemplary embodiment, each of the first sensors 204 can be configured to simultaneously collect sensor data related to NH3 concentrations as the agricultural apparatus 120 travels over the worksite 155. For example, as depicted, the unmanned aerial vehicle 203 can be arranged to fly in proximity to the agricultural apparatus 120, and utilizing the first sensor 104, can sense and monitor vapors (i.e., NH3) being emitted from the soil as the crop material is being applied to soil via the applicator devices 128.

In some embodiments, the unmanned aerial vehicle 203 can comprise onboard processing/power components (not shown) and a propulsion system 206 that allows for the unmanned aerial vehicle 203 to be autonomously or operator controlled, and allows for the vehicle 125 to communicate wirelessly with the agricultural apparatus 120. For example, the propulsion system 206 and the onboard processing components can be used to control the direction, height, attitude, speed, and other characteristics of the unmanned aerial vehicle 203. In other embodiments, the unmanned aerial vehicle 203 can be optionally coupled directly to the agricultural apparatus 120 via a tether link 210 as shown in FIG. 3. For example, in some embodiments, the unmanned aerial vehicle 203 can be coupled to agricultural implement 124, the agricultural vehicle 125, or the reservoir 132 by the tether link 210, which provides power and communication links from the agricultural apparatus 120 to unmanned aerial vehicle 203. In yet other embodiments, the unmanned aerial vehicle 203 can also comprise an onboard positioning system that provides geographical information to indicate the relative positions of agricultural apparatus 120 and unmanned aerial vehicle 203.

Figure 4:
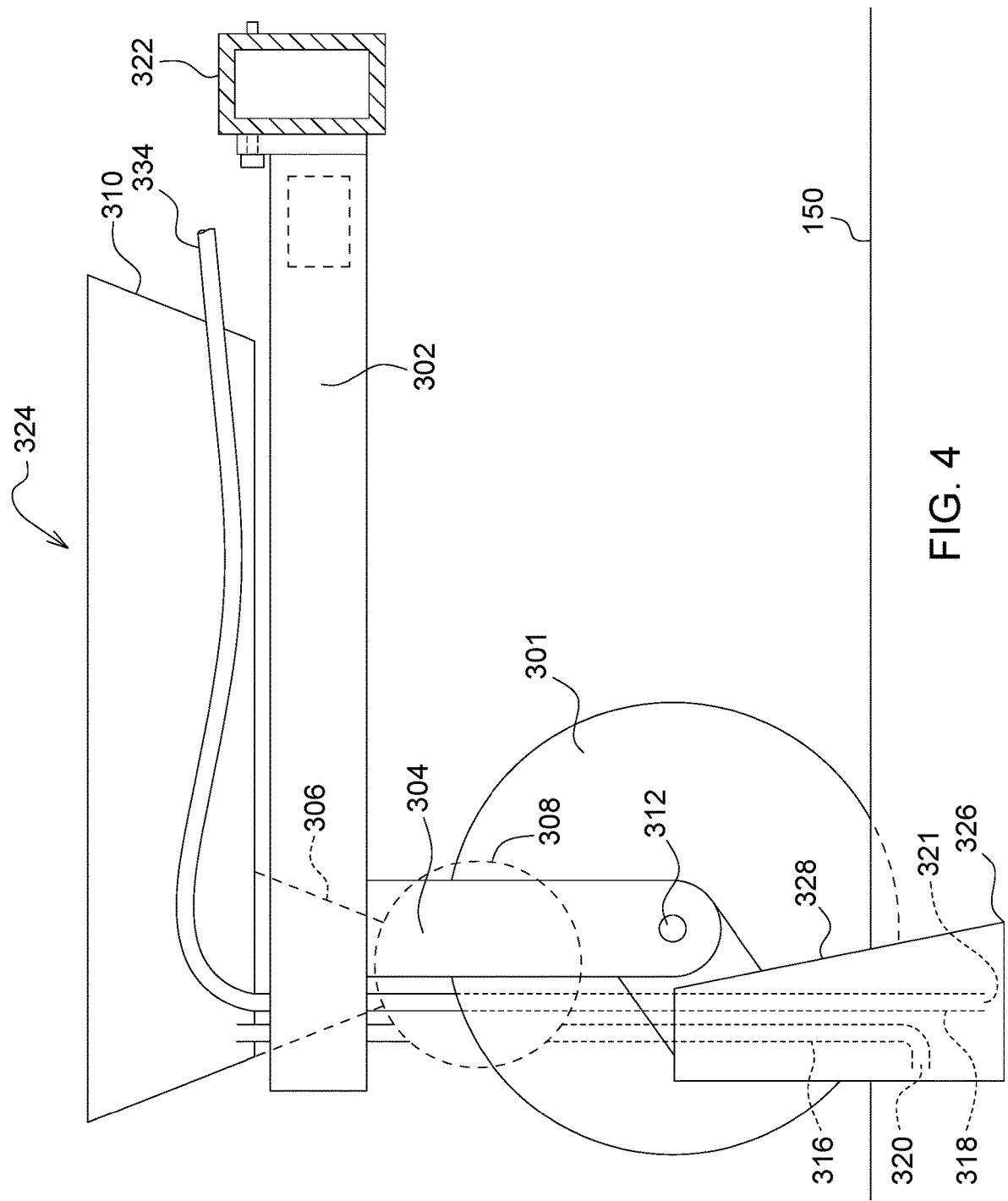
FIG. 4 is a side view of a row unit or ground-engaging member of an agricultural implement arranged in the agricultural apparatus of FIGS. 1 and 3 according to an embodiment.

In FIG. 4A, a side view of an agricultural implement 324, which is an alternative embodiment of the agricultural implement 124, is shown. In various applications, the agricultural implement 324 can be used to replace the agricultural implement 124. In this exemplary embodiment, seeds and nutrients may be applied simultaneously to the soil 150. As depicted, each ground engaging assembly 314 (e.g., a row unit) of the agricultural implement 324 can comprise a hopper 310 coupled to a beam assembly 302 that is arranged to supply non-aqueous or non-vaporized crop input materials such as seeds. An inlet port 306 of a seed metering device 308 is arranged between the hopper 310 and the second outlet 320. A first support member 304 can be coupled to or integral with the frame 322. The first support member 304 extend downward from the frame 322. A ground engaging disc 301 is supported by or from the first support member 304. In one embodiment, the ground engaging disc 301 is rotatable with respect the first support member 304; the ground engaging disc 301 may be mounted to the first support member 304 via radial bearing or shaft 312 at a hub of the ground engaging disc 301. However, in an alternate embodiment the ground engaging disc 301 may be fixed or non-rotating with respect to the first support member 304.

As previously discussed, in some embodiments, the applicator device 328 can be arranged proximate the ground engaging disc 301 and can track or follow a path of the ground engaging disc 301. As depicted, the applicator device 328 or sharp, pointed member may be connected to or extend from the first support member 304. As illustrated the applicator device 328 (applicator device 328) has a pointed leading edge 324 for forming or carving a groove in the soil 150.

In some embodiments, the applicator device 328 may comprise a first conduit or tube 318 that terminates a first outlet 321 (e.g., treatment opening) for directing nitrogen, ammonia or other nutrient into the soil that the applicator device 328 can displace after the opener. From a reservoir, such as reservoir 132, at least one of the dispensing elements 334 is connected to the first tube 318 for delivery of NH3, nutrients, nitrogen, fertilizer or other crop input materials from a reservoir. The applicator device 328 can comprise a second conduit or tube 316 that terminates in a second outlet 320 for seed deposition into the soil 150 within or spaced apart from the groove by a vertical separation between the first outlet 321 and the second outlet 320. In other embodiments, the first outlet 321 and the second outlet 320 have one or more of the following separations: a lateral separation, a vertical separation and longitudinal separation, wherein seed and nutrients may be applied simultaneously to the soil consistent with the separations.

In other embodiments, the applicator device 328 can comprise a dual tube arrangement (not shown) that is arranged separate from the seed tube which allows for fertilizer to be applied simultaneously with smaller grain seeds. For example, in such embodiments, the dual tube arrangement can comprise a first tube that is configured to supply a first fertilizer such as anhydrous ammonia, and a second tube that is configured to supply a second fertilizer such as ammoniated phosphate.

Figure 5:
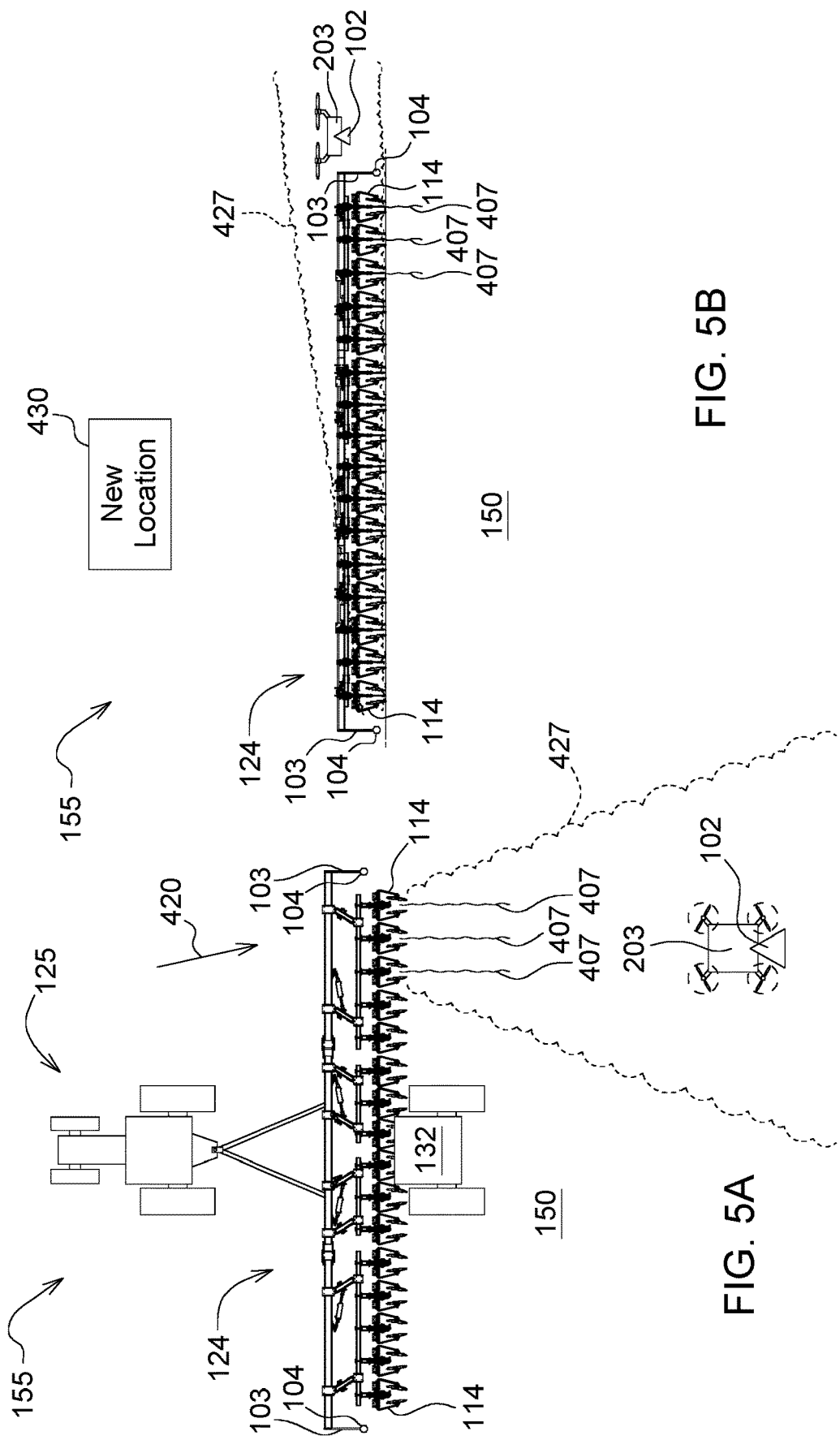
FIG. 5A is a plan view of an exemplary embodiment of a sensor system for monitoring vapor concentrations in use with an agricultural apparatus.
FIG. 5B is a plan view of an exemplary embodiment of a sensor system for monitoring vapor concentrations in use with an agricultural apparatus.

Referring to FIGS. 5A and 5B, an illustration of the sensor system 200 in use with the agricultural apparatus 120 is shown. As depicted, as the crop material is applied to the worksite 155 by the applicator devices 128, the crop material can include a material that quickly transitions from liquid to a vaporized material 407 at normal outdoor temperatures, which, in this example, the vaporized material 407 includes anhydrous ammonia (i.e., $NH_3$). A three dimensional plume 427 (i.e., a vapor concentration area) is formed by the emissions of the vaporized material 407, and travels in a direction away from the agricultural implement 124. The location and emission direction of the plume 427 can and will vary in various applications based, without limitation, on a wind direction, wind speed, implement direction, implement speed, and ambient air temperature. For example, as depicted in FIG. 5A, the wind is blowing in from the northwesterly direction indicated by the arrow 420 (e.g., from an upper left direction to a lower right direction), which thereby causes the plume 427 to form in an area generally southeast of the agricultural apparatus 120.

The first sensor 104, which, as previously discussed, can be arranged on the support arm 103 and/or the unmanned vehicle 125, is configured to sense a concentration of at least one component of a vapor sample (i.e., $NH_3$) emitted from the soil 150 into the atmosphere at a location of the plume 427. For example, as previously discussed, the first sensor 104 can comprise one or more infrared sensors that can include infrared optical gas imagers that are configured to sense concentrations of the at least one component of the vapor sample by emitting an infrared radiation energy source into the vapor sample.

Figure 6:
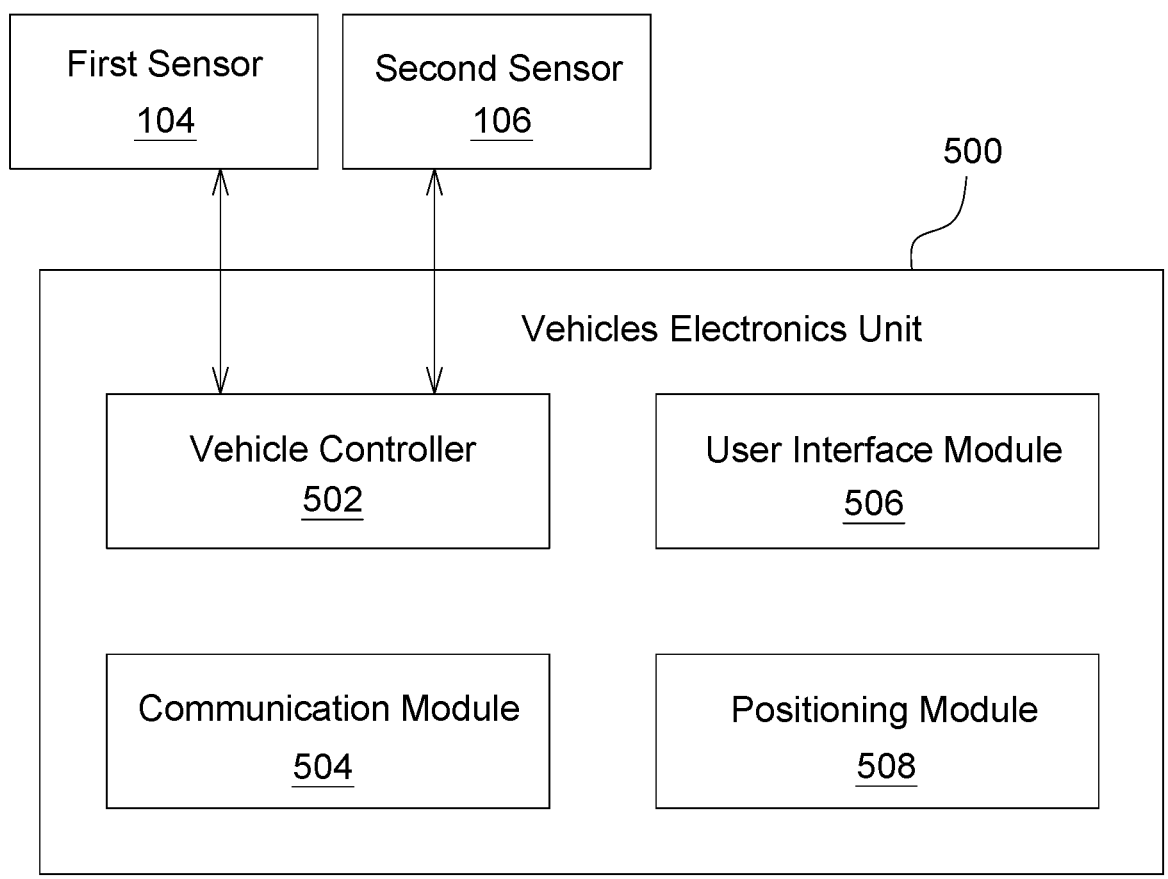
FIG. 6 is a block diagram an exemplary embodiment of a vehicle electronics unit arranged in the agricultural apparatus of FIGS. 5A and 5B.

As discussed with reference to FIGS. 1 and 3, this data is measured collectively with the one or more soil attributes sensed by the second sensor 106 and is communicated to the controller 108, which may include a controller arranged locally on the unmanned aerial vehicle 203 and/or included in a vehicle electronics unit 500 of the agricultural apparatus 120. For example, as depicted in FIG. 6, the vehicle electronics unit 500 having a vehicle controller 502 illustratively receives data from the first sensor 104 and the second sensor 106. In addition to the vehicle controller 502, the vehicle electronics unit 500 can further comprise a communication module 504, one or more user interface modules 506, and a positioning module 508.

The communication module 504 can communicate the output signals generated by the first sensor 104 and the second sensor 106 to the vehicle controller 502 to the one or more user interface modules 506. For example, based on the received sensor data, the one or more user interface modules 506 can be configured to generate an alert signal that is displayed on a user interface (not shown) for view by an operator of the agricultural vehicle 125. In other embodiments, agricultural vehicle 125 may be autonomous and the alert signal is used to stop or adjust application, possible in conjunction with data from second sensor 106. In other embodiments, the communication module 504 can also be configured to communicate the position of the unmanned aerial vehicle 203 identified by the positioning module 508, or other additional information such as, e.g., crop related properties sensed by the second sensor 106. The positioning module 508 can be configured to generate a position indicator indicating a position of the agricultural apparatus 120. For example, the positioning module 508 can include a global position system (GPS), a dead reckoning system, a cellular triangulation system, or a wide variety of other positioning systems.

Figure 7:
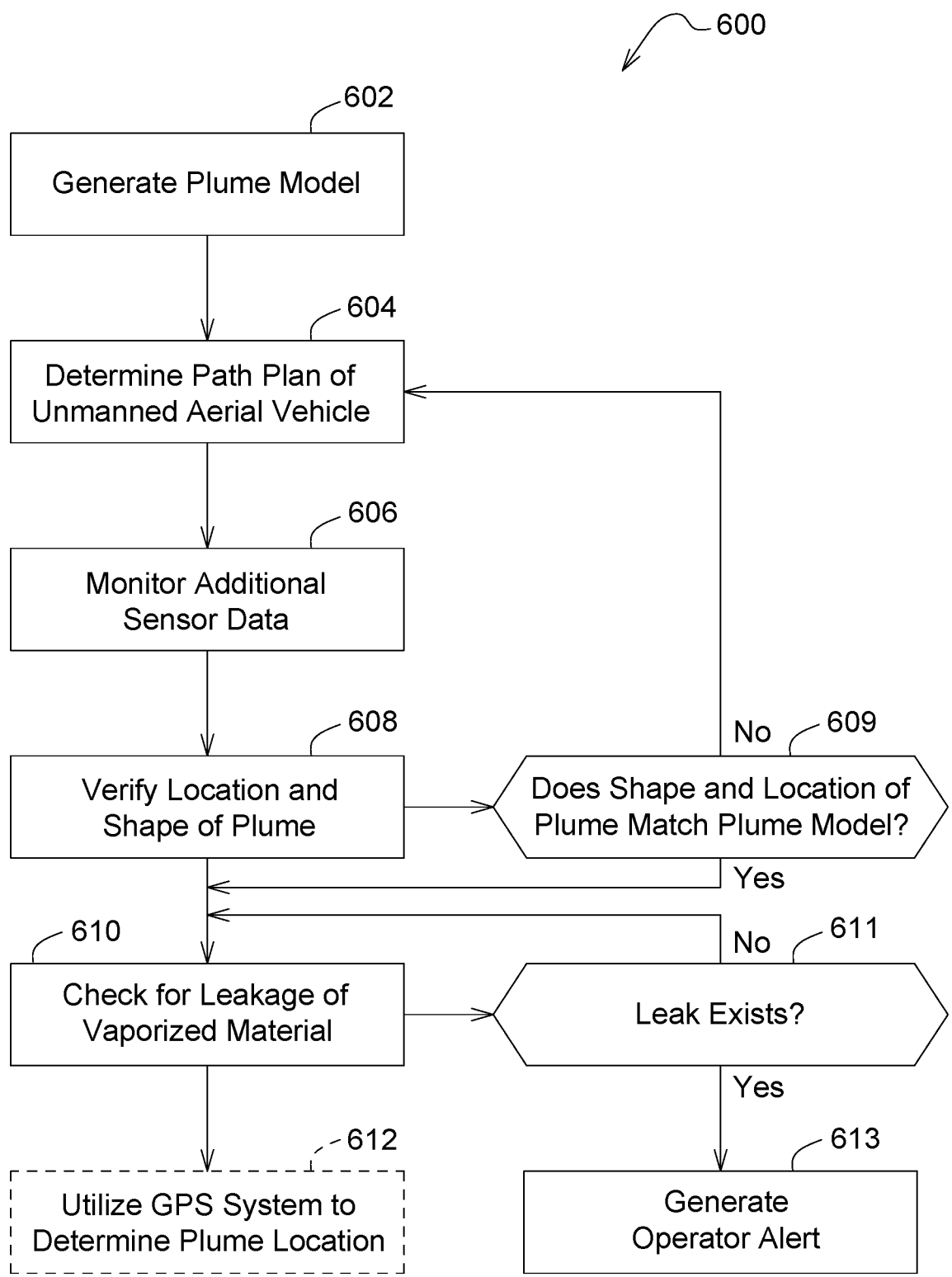
FIG. 7 is flow diagram of a method for monitoring vapor concentrations.

Referring now to FIG. 7, a flow diagram of a method 600 for monitoring vapor concentrations is shown. Notably, with the present disclosure, the problem of knowing net soil nitrogen fertilizer application levels is solved, at least in part, through the use of the first sensor 104 and the unmanned aerial vehicle 203. For example, by flying the unmanned aerial vehicle 203 equipped with the first sensor 104 over a field to trail an implement that is applying NH3 to the soil during application of the NH3 to collect atmospheric NH3 concentration and associated data can accurately measure and model nitrogen (N) loss. As will be discussed below, in some embodiments, the measured level of escaped NH3 can also be used as a feedback signal that is used to adjust an implement parameter related to closing or sealing the NH3 into the ground or ultimately signaling that NH3 application should be halted.

The method of FIG. 7 begins in step 602. At block 602, a plume model can be generated by the controller 108 based on a variety of sensor or implement data such as information related to the position, location, or depth of the ground engaging elements 114, vapor attributes, measured vapor concentration, wind velocity, etc. For example, utilizing the generated plume model, the shape and location of the plume 427 can be determined, which can be used to guide the unmanned aerial vehicle 203 with respect to the location of the plume 427. In some computations, measured data such as vapor concentration levels may be weighted more heavily than in other examples, including those which do not consider vapor concentrations.

Next, at 604, the controller 108 uses plume information, as well as other information (e.g., weather, wind direction, precipitation, temperature, soil conditions, etc.) to determine a path plan for the unmanned aerial vehicle 203. For example, in one embodiment, the path plan of the unmanned aerial vehicle 203 can be computed utilizing the location and shape of plume 427, such that the unmanned aerial vehicle 203 and its sensors fly or travel within the plume 427 at one or more three dimensional sampling points associated with the plume 427 to make measurements indicative of leakage of the NH3 vapor or vaporized material. In other embodiments, the path plan of the unmanned aerial vehicle 203 can be used as a control signal that causes the unmanned aerial vehicle 203 to exit the plume 427 based on the identified plume location and shape. In still other embodiments, the path plan of the unmanned aerial vehicle 203 can also be used by the controller 108 to control sampling of the vaporized material 407 in plume 427 using the first sensor 104.

At 606, additional measurements can be taken by the first sensor 104 and communicated to the controller 108. For example, continuous measurements can be taken to comparatively analyze the location and shape of the plume 427 with the plume model, as well as to ensure that excess vaporized material 407 is not generated from escaping NH3 from the soil or any leaks (e.g., at tubes or fittings) of the vaporized material 407 between the reservoir 132 and the ground engaging elements 114.

Once the measurements are taken, the shape and location of the plume 427 is verified based on the generated plume model at 608. Next at 609, a determination is made as to whether or not any deviation exists between the actual location of the plume 427 and the plume model. If deviations exist, the path plan of the unmanned aerial vehicle 203 is again determined at 604. For example, the controller 108 generates a control signal that is received by the propulsion system 206 to adjust the location and height of unmanned aerial vehicle 203 for positioning within the plume 427. Additionally, during 180 degree turns of the agricultural vehicle 125 and the attached agricultural implement 124, the path plan of the unmanned aerial vehicle 203 can be adjusted to place the unmanned aerial vehicle 203 in a predicted new location 430 as shown in FIG. 5B. At 610, the sensor system 200 further verifies that there are not any leaks or excess material presence. A determination is made at 611 and if either condition exists, the controller 108 can be configured to generate an operator alert at 613. In other embodiments, the controller 108 can be further configured to generate a control signal that adjusts a height or position of the ground engaging elements 114 or the applicator devices 128. For example, some of the adjustment parameters can include, but is not limited to, a ground engaging element height above ground; a ground engaging element depth into or below ground, down-pressure, or angle; chemical application type or rate; chemical application pattern; or other suitable mechanism controls.

Optionally at 612, in some embodiments, the unmanned aerial vehicle 203 can further comprise a location determining device such as a localization sensor (not shown) that receives GPS and other positioning signals from a global navigation satellite system. The GPS/positioning can be used collectively with the path plan to guide unmanned aerial vehicle 203. As will be appreciated by one skilled in the art, global navigation satellite systems and radio-triangulation systems are two non-limiting examples of tracking and/or positioning systems.

Without in any way limiting the scope, interpretation, or application of the claims appearing below, a technical effect of one or more of the example embodiments disclosed herein is a system and method for monitoring vapor concentrations. Notably, the system and method of the present disclosure significantly improves the efficacy of fall NH3 application by providing a system that is capable of accurately measuring NH3 escaping from the soil at the time of application. For example, the sensor data can be used to stop an application where too much NH3 is being lost to the soil, decrease escape by adjusting application equipment based on the escape data, or to adjust a future nitrogen (N) application based on amount of NH3 successfully sealed into the soil.

While the present disclosure has been illustrated and described in detail in the drawings and foregoing description, such illustration and description is not restrictive in character, it being understood that illustrative embodiment(s) have been shown and described and that all changes and modifications that come within the spirit of the present disclosure are desired to be protected. Alternative embodiments of the present disclosure may not include all of the features described yet still benefit from at least some of the advantages of such features. Those of ordinary skill in the art may devise their own implementations that incorporate one or more of the features of the present disclosure and fall within the spirit and scope of the appended claims.

What is claimed is:

1. A sensor system for monitoring vapor concentrations associated with an agricultural implement, the sensor system comprising:
   a first sensor coupled to a support structure of an unmanned aerial vehicle, wherein the first sensor is configured to sense a concentration of at least one component of a vapor sample emitted from soil, where the vapor sample is associated with dispensed ammonia; and
   a controller communicatively coupled to the first sensor, wherein the controller is configured to:
   receive and process output signals generated by the first sensor to determine an amount of the concentration of the at least one component that is lost during emission, wherein if the loss exceeds a certain threshold level, an alert is displayed or communicated to an operator of the agricultural implement; and
   generate a plume model based on the signals generated by the first sensor, wherein the plume model includes the determined amount of the component concentration, the plume model used to determine a path plan for the unmanned aerial vehicle.

2. The sensor system of claim 1 further comprising at least one second sensor, wherein the at least one second sensor is configured to generate an output signal indicative of a measured soil attribute.

3. The sensor system of claim 2, wherein the second sensor is configured to measure one or more of the following: snow cover, thermal latency, soil temperature, soil type, bulk soil density, soil moisture, or combinations thereof.

4. The sensor system of claim 2 further comprising a localization sensor that is configured to determine a position of the first sensor and the second sensor and their respective measurement data.

5. The sensor system of claim 1, wherein the support structure is arranged on or proximate the agricultural implement, and wherein the agricultural implement is arranged to dispense ammonia with respect to a direction of forward travel of the agricultural implement.

6. The sensor system of claim 5, wherein the support structure comprises a support arm arranged to extend backwards from a ground engaging element attached to the agricultural implement, and wherein the agricultural implement is configured to perform a task simultaneously with application of ammonia.

7. The sensor system of claim 5, wherein the support structure trails or follows a closer or firming wheel of a row unit.

8. The sensor system of claim 1, wherein the unmanned aerial vehicle is arranged to aerially hover above the soil proximate a vapor emission area.

9. The sensor system of claim 1, wherein the first sensor comprises one or more of the following: a piezoelectric sensor, an ultrasonic sensor, an infrared sensor, infrared optical gas imaging sensor, an acoustic sensor, a laser spectrometer, non-equilibrium electrochemical principal sensor, or combinations thereof.

10. The sensor system of claim 1, wherein the vapor sample comprises anhydrous ammonia.

11. The sensor system of claim 1, wherein the at least one component of the vapor sample comprises gaseous components associated with ammonia or nitrogen application.

12. The sensor system of claim 1, wherein the controller is further configured to adjust an operating parameter of the agricultural implement, the operating parameter including an application quantity of the dispensed ammonia, based on the determined concentration loss.

13. The sensor system of claim 1, wherein the controller is further configured to adjust an operating parameter of the agricultural implement, the operating parameter including downforce pressure or depth of an applicator device that dispenses the ammonia, based on the determined concentration loss.

14. A method for monitoring vapor concentrations, the method comprising:
    positioning a first sensor proximate a vapor emission area, the first sensor positioned on an unmanned aerial vehicle;
    detecting a concentration of a vapor component of a vapor sample emitted from the vapor emission area; and
    determining an amount of the concentration of the vapor component that is lost during emission of the vapor sample; and
    generating a plume model based on the determined amount of the component concentration, the plume model used to determine a path plan for the unmanned aerial vehicle.

15. The method of claim 14 further comprising sensing at least one soil attribute with a second sensor as the concentration of the vapor component is detected, wherein the sensed soil attribute and the detected concentration of the vapor component are georeferenced to specific field locations in which the first sensor and the second sensor are located.

16. The method of claim 15, wherein the vapor sample comprises anhydrous ammonia, and wherein the concentration of the vapor component is detected simultaneously as the anhydrous ammonia is applied.

17. The method of claim 14, wherein detecting a concentration of a vapor component of a vapor sample comprises emitting an infrared radiation energy source into the vapor sample to detect a concentration of the vapor component.

18. The method of claim 14, wherein determining an amount of the concentration of the vapor component comprises determining a concentration of one or more gaseous components associated with ammonia or nitrogen application.

19. The method of claim 14 further comprising adjusting an operating parameter of an agricultural implement based on the determined amount of the concentration of the vapor component that is lost during emission of the vapor sample.

20. The method of claim 14 further comprising displaying an alert or communicating to an operator of the agricultural implement when the determined loss exceeds a certain threshold level.

* * * * *